United States Patent [19]
Dissaux et al.

[11] Patent Number: 5,518,703
[45] Date of Patent: May 21, 1996

[54] PRODUCTION OF FINELY DIVIDED RARE EARTH AMMONIUM OXALATES/FINELY DIVIDED RARE EARTH OXIDES

[75] Inventors: Bernard-Antoine Dissaux, Chagnolet par Dompierre S/Mer; Jean-Luc Le Loarer, La Rochelle; Bernard Pacaud, Nanterre; Michel Ries, Vitry sur Seine, all of France

[73] Assignee: Rhone-Poulenc Chimie, Courbevoie, France

[21] Appl. No.: 237,415

[22] Filed: May 3, 1994

Related U.S. Application Data

[63] Continuation of Ser. No. 696,152, May 6, 1991, abandoned.

[30] Foreign Application Priority Data

May 4, 1990 [FR] France ................................. 90 05654

[51] Int. Cl.$^6$ ................................ C01F 17/00; C07F 5/00
[52] U.S. Cl. ............................................... 423/263; 534/16
[58] Field of Search ..................................... 423/21.1, 263, 423/592; 252/301.4 R; 534/16

[56] References Cited

U.S. PATENT DOCUMENTS

| | | | |
|---|---|---|---|
| 4,375,453 | 3/1983 | Nalewajek et al. | 423/21.1 |
| 4,891,163 | 1/1990 | Tanaka et al. | 252/627 |

FOREIGN PATENT DOCUMENTS

| | | |
|---|---|---|
| 2145820 | 3/1972 | Germany. |
| 53-95911 | 8/1978 | Japan. |
| 55-28905 | 2/1980 | Japan. |
| 1208565 | 10/1970 | United Kingdom. |
| 2205090 | 11/1988 | United Kingdom. |

OTHER PUBLICATIONS

M. F. Barrett, T. R. R. McDonald and N. E. Topp, "Double Ammonium Oxalates of the Rare Earths and Yttrium", J. Inorg. Nucl. Chem., 1964, vol. 26, pp. 931–936.

T. R. R. McDonald and Jennifer M. Spink, "The Crystal Structure of a Double Oxalate of Yttrium and Ammonium, $NH_4y(C_2O_4)_2.H_2O$", Acta Cryst., 1967, vol. 23, pp. 944–949.

Yukinori Minagawa and Fumikazu Yajima, "New Preparative Method of Fine Powder of Yttrium (III) Oxide by Thermal Decomposition of $NH_4Y(C_2O_4)_2.H_2O$ Fine Crystal Obtained by Reaction of a Strongly Acidic Solution of Yttrium Oxalate and an Aqueous Ammonia Solution", Bull. Chemical Society of Japan, 1990, vol. 63, pp. 378–382.

Yukinori Minagawa and Fumikazu Yajima, "Preparative Method of Fine Powder of Yttrium (III) Oxide by Thermal Decomposition of $NH_4Y(C_2O_4)_2.H_2O$ Fine Crystals Obtained by New Reaction of Yttrium (III) Hydroxide Slurry with Acid Solution", Bull. Chemical Society of Japan, vol. 63, pp. 2115–2117, 1990.

Patent Abstracts of Japan, vol. 4, No. 61 (C–9) [543], 8 May, 1980 JP-A-55 28 905 (Mitsubishi Kasei Kogyo) 29-2-1980.

Primary Examiner—Steven Bos
Attorney, Agent, or Firm—Burns, Doane, Swecker & Mathis

[57] ABSTRACT

Very finely divided ammonium rare earth double oxalates, readily converted into corresponding rare earth oxides by calcination, such oxides being well adopted, e.g., for the production of luminescent compounds therefrom, are prepared by (a) admixing a second solution of a rare earth compound, e.g., a salt, with a first solution containing oxalate and ammonium ions, (b) then separating the precipitate thus obtained from such mixed solution of reaction, and (c) optionally, drying the separated precipitate.

23 Claims, 1 Drawing Sheet

PRODUCTION OF FINELY DIVIDED RARE EARTH AMMONIUM OXALATES/FINELY DIVIDED RARE EARTH OXIDES

This application is a continuation of application Ser. No. 07/696,152, filed May 6, 1991, now abandoned.

BACKGROUND OF THE INVENTION

1. Field of the Invention

The present invention relates to the preparation of rare earth ammonium double oxalates and to the production of rare earth oxides therefrom.

This invention especially relates to the preparation of such double oxalates having a well defined morphology and particle size.

2. Description of the Prior Art

The rare earth oxides find numerous applications, particularly in the field of ceramics and electronics, but there currently exists an increasing demand for such products having a controlled particle size.

One of the conventional processes for preparing rare earth oxides which is widely described in the literature, in particular in Paul Pascal's *Nouveau Traite de Chimie Minerale*, Vol. III, p. 1007 (1959), entails calcining, at a temperature ranging from 500° to 900° C., the rare earth oxalates obtained by precipitation of the corresponding rare earth salts in the form of an aqueous solution by means of oxalic acid. However, a process of this type produces particulates of rare earth oxides having a large particle size.

It has also been described, in JP-A 53/095,911 (*Chemical Abstracts*, 90, 40940 w), to prepare finely divided rare earth oxides and, more particularly, finely divided yttrium oxide, by calcination of a yttrium ammonium oxalate, which entails providing an aqueous solution of a yttrium salt as the starting material, precipitating the yttrium in the form of its hydroxide by reaction of the aqueous solution of the yttrium salt with a basic aqueous solution such as ammonia, then treating the resultant hydroxide slurry with oxalic acid and finally separating off the precipitate thus obtained, washing it and calcining the precipitate at a temperature of 750° C. According to this JP-A 53/095,911, such process produces finely divided yttrium oxide. The diameter of the particles is said to range from 0.9 to 4.5 µm, the crystals having the shape of platelets with rounded edges.

However, the size of these particles is still relatively large relative to the dimensions required for certain applications such as luminescence. Moreover, monitoring the size of the particles is relatively difficult because the conditions for actually carrying out the process have a substantial influence on the particle size.

SUMMARY OF THE INVENTION

Accordingly, a major object of the present invention is the provision of an improved process for the production of particulates of ammonium rare earth double oxalates having a narrow particle size distribution with average particle sizes of the crystals which can extend to less than one micron, and which improved process otherwise avoids or conspicuously ameliorates the above disadvantages and drawbacks to date characterizing the state of this art.

By the term "rare earth ammonium double oxalate" is intended a compound comprising one or more rare earths that is converted into simple or mixed oxides upon calcination thereof.

Briefly, the present invention features a process for the production of a rare earth ammonium double oxalate, comprising (a) adding a second solution of a rare earth compound to a first solution containing oxalate and ammonium ions, (b) separating off the precipitate thus obtained, and, (c) optionally, drying such precipitate.

DETAILED DESCRIPTION OF THE PREFERRED EMBODIMENTS OF THE INVENTION

Figure 1:
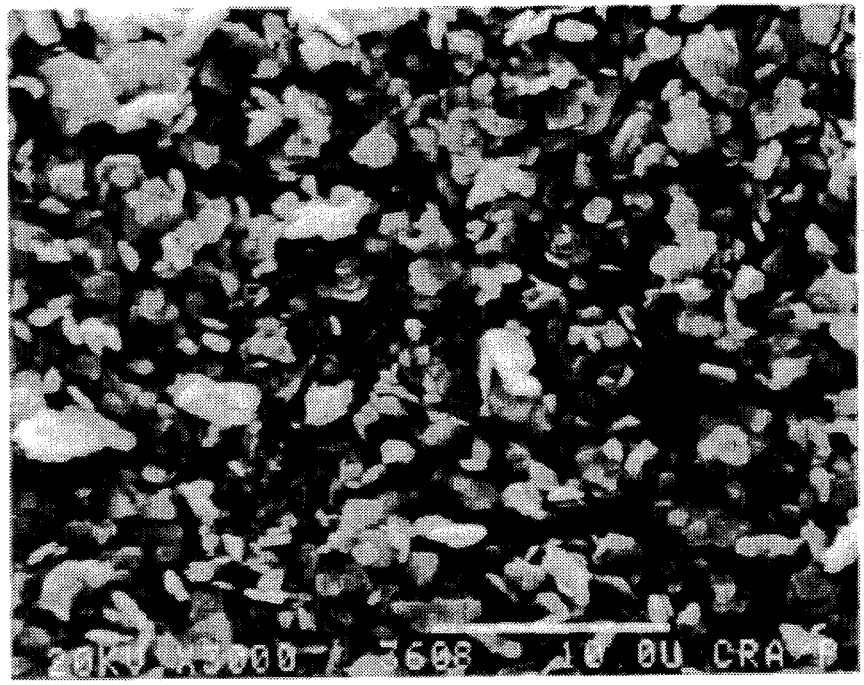
FIG. 1 is a photomicrograph showing the morphology of a rare earth ammonium double oxalate according to the present invention.

More particularly according to the present invention, in a preferred embodiment thereof, the rare earth compound is advantageously a soluble compound, such as a rare earth salt.

Exemplary such salts include the chlorides, nitrates, sulfates or acetates of scandium, yttrium, lanthanum, cerium, praseodymium, neodymium, samarium, europium, gadolinium, terbium, dysprosium, hafnium, erbium, thulium, ytterbium, lutetium, or mixture thereof. In particular, it is possible to use an aqueous solution containing rare earth salts which directly or indirectly emanates from the treatment and processing of rare earth ores.

Although the process of the invention is notably applicable to the cerium rare earths, it is more particularly suitable for the yttrium rare earths.

By the term "cerium rare earths" are intended the lightest of the rare earths, commencing with lanthanum and extending to neodymium according to atomic number, and the heaviest of the rare earths according to the atomic number, commencing with samarium and extending to lutetium and including yttrium, are designed "yttrium rare earths".

The concentration of the rare earth compound is not critical.

The aforesaid second solution is an aqueous solution, the pH of which may be adjusted to an established value or an established range by addition of buffer solution or of acids thereto, if such is necessary. In general, this second solution essentially contains one or more rare earth compounds.

Exemplary of these acids are the inorganic acids such as nitric acid.

The aforesaid first solution contains ammonium and oxalate ions provided in the form of one or more salts containing these two species, such as, for example, ammonium oxalate or ammonium hydrogen oxalate, or by a mixture of compounds, each supplying one of the two species ammonium or oxalate. Thus, the various ammonium salts, such as ammonium nitrate or ammonium chloride, or even ammonia in the form of a gas or in solution, are well adopted for the addition of the ammonium ion.

With regard to the oxalate species, the various metal oxalates, such as sodium oxalate for example, and preferably oxalic acid, are exemplary.

The concentration of $(C_2O_4)^=$ and $NH_4^+$ ions in the solution is also not critical and may vary over wide limits.

In a preferred embodiment of the invention, the oxalate and ammonium concentrations and also the rare earth concentration in the second solution and the volumes of the first and second solution will be determined such as to provide, upon completion of the addition of the second solution, a molar ratio between the oxalate ion and the rare earths $((C_2O_4)^=/RE)$ higher than or equal to 2, advantageously higher than 2.5, and an ammonium to rare earths ratio $(NH_4^+/RE)$ higher than or equal to 2, preferably higher than 2.5.

In another preferred embodiment of the invention, the first solution is an aqueous solution of ammonium oxalate.

In another preferred embodiment of the invention, the first solution is an aqueous solution of ammonium oxalate and oxalic acid. Advantageously, the molar ratio $((C_2O_4)^=/NH_4^+$ is higher than 2 and between 2 and 4.

In still another preferred embodiment of the invention, the first solution is an aqueous solution of ammonium oxalate and ammonia; the ratio $C_2O_4^=/NH_4^+$ must be higher than 0 and advantageously ranges from 0.4 to 2.

This first solution may also comprise an inorganic acid (HA), such as nitric acid, for example, it being possible for this acid to be added to a solution of ammonium oxalate or liberated in situ by the addition of oxalic acid to a solution of ammonium salts, for example of ammonium nitrate.

When an inorganic acid HA is present in the first or second solution, the amount of HA acid employed is determined such as to provide a molar ratio of the anion A– of said acid relative to the total amount of oxalate of below 5.

The conditions for carrying out the process of the invention are not very critical in order to produce a double oxalate. However, controlling the rate of introduction of the second solution, the temperature and the agitation of the mixture permits the morphology of the double oxalate precipitated to be modified and controlled.

It is also possible to carry out the process of the invention in a continuous manner by continuously mixing the first and second solutions described below.

Moreover, the temperature has an influence on the precipitation yield because the solubility coefficient of the double oxalate increases as the temperature increases.

The precipitate obtained is separated from the supernatant liquid by any solid/liquid separation technique, such as, for example filtration, centrifuging, settling or the like. It may also be subjected to one or more washings in order, for example, to remove the soluble salts.

The rare earth ammonium double oxalate may be subjected to drying in order to evaporate the unbonded water, for example by a heat treatment at a temperature ranging from 50° C. to 100° C., or a drying under reduced pressure.

The rare earth ammonium double oxalate produced by the process of the invention is particulate, the shape and size of the particles depending on the nature and on the pH of the solutions, as well as on the temperature and agitation conditions and the rate of introduction during mixing of the solutions.

Thus, in the event that the first solution is an ammonium oxalate solution, the final particles are in the form of platelets of small thickness (thickness equal to about 0.3 μm) and having an average particle size ranging from 0.5 μm to 3 μm, advantageously from 0.5 μm to 1 μm, and more advantageously from 05. μm to 0.9 μm.

In the event that the first solution is a solution of a mixture of oxalic acid and ammonia or another ammonium compound, with the exception of ammonium oxalate, the average size of the particles ranges from 1 μm to 5 μm. These particles are in the essentially cubic form.

The process of the invention enables a rare earth ammonium double oxalate to be produced which has a homogeneous particle size. Thus, the particle size distribution of the crystals is very narrow. The dispersion coefficient of the crystal sizes is generally below 0.7 and advantageously ranges from 0.2 to 0.6.

The dispersion coefficient is determined by the ratio $$\frac{\phi_{84} - \phi_{16}}{2\phi_{50}}$$

in which $\phi_{84}$ $\phi_{16}$ $\phi_{50}$ represent the diameters of the particles corresponding to 84%, 16% and 50% thereof. Advantageously, the particle size dispersion coefficient is <0.7.

One of the uses of these rare earth ammonium double oxalates is for the production of rare earth oxides, by thermal decomposition of such oxalates.

The morphology and particle size of the rare earth oxides obtained by decomposition of a double oxalate is generally similar to that of the double oxalate used as the precursor therefor. However, depending on the heat treatment conditions for the double oxalate, the particle size of the oxide may differ slightly from that of the oxalate.

The heat treatment, or calcination, is typically carried out at a temperature ranging from 600° to 1,200° C., advantageously from 800° to 1,000° C.

The calcination time is determined in conventional manner by monitoring to constant weight. For example, the calcination time may range from about 30 minutes to 6 hours.

In order to further illustrate the present invention and the advantages thereof, the following specific examples are given, it being understood that same are intended only as illustrative and in nowise limitative.

EXAMPLE 1

A solution of yttrium nitrate having a concentration of 170 g/l, expressed as $Y_2O_3$, was added to solutions of ammonium oxalate of varying concentrations below 0.9M.

A series of experiments was carried out using such solutions, the results of which are reported in Table I below.

The size and the particle size distribution of the products obtained were determined using a SEDIGRAPH 5000D instrument, which determines the rate of sedimentation of the particles in suspension and determines the particle size distribution in cumulative percentages as a function of the equivalent spherical diameters. This determination was based on STOKE's law.

TABLE I

| Ratio $NH_4/Y$ | [Y] $gY_2O_3/l$ (1) | $S_{50}$ μm | Particle size dispersion coefficient |
|---|---|---|---|
| 5 | 5 | 0.69 | 0.57 |
| 5 | 17 | 0.84 | 0.47 |
| 6 | 17 | 0.80 | 0.35 |
| 8 | 17 | 0.64 | 0.53 | wherein [Y]: total concentration of yttrium in the reaction mixture, expressed as $Y_2O_3$
$S_{50}$: average size of the rare earth oxide obtained by calcination of the double oxalate (900° C. for 1 hour).

The particles had a platelet shape of fairly irregular contours.

EXAMPLE 2

This series of experiments was carried out using a second solution of yttrium nitrate identical to that of Example 1, but using a first solution containing a mixture of $(NH_4)_2C_2O_4$ and $H_2C_2O_4$.

The results and ratios between the various species employed are reported in Table II. The Y concentration in the reaction mixture was 17 g/l as $Y_2O_3$.

TABLE II

| $C_2O_4^=/Y$ | $NH_4^+/Y$ | $S_{50}$ oxide | Particle size distribution coefficient (F) |
|---|---|---|---|
| 2.5 | 2.5 | 0.90 | 0.46 |
| 3.0 | 3.0 | 1.15 | 0.67 |
| 4.0 | 5.0 | 1.1 | 0.40 |

Figure 2:
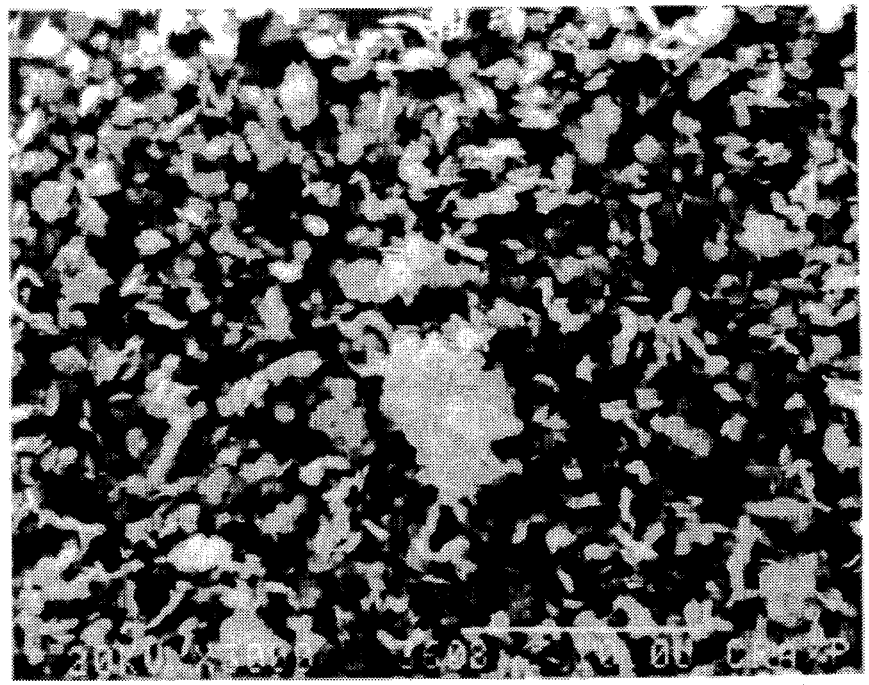
FIG. 2 is a photomicrograph showing the morphology of the rare earth oxide prepared by calcining the double oxalate illustrated in FIG. 1.

The double oxalate crystals obtained were in the form of platelets having a thickness of about 0.3 μm and average sizes of 0.7 to 1 μm. The morphologies of the oxalate and of the calcined oxide are illustrated in FIGS. 1 and 2, respectively.

EXAMPLE 3

The experiments were identical to those of Example 2, but using a first solution which comprised ammonia and oxalic acid.

The results and ratios between the various species are reported in Table III (final yttrium concentration: 17 g/l as $Y_2O_3$):

TABLE III

| $C_2O_4^=/Y$ | $NH_4^+/Y$ | $S_{50}$ oxide | Particle size dispersion coefficient (F) |
|---|---|---|---|
| 4.0 | 3.0 | 1.5 | 0.37 |
| 2.5 | 5.0 | 0.75 | 0.47 |

EXAMPLE 4

A yttrium nitrate solution containing 150 g/l, expressed as $Y_2O_3$, and 0.8 mol/l of nitric acid was added to a 25 g/l ammonium oxalate solution. The amount of solution employed was determined such as to provide a ratio between the ammonium oxalate and the rare earth salt 10% higher than the stoichiometric ratio.

After separating off, drying and calcining the resulting ammonium yttrium oxalate, a yttrium oxide was obtained which had a $S_{50}$ of 2 μm and a particle size dispersion index (F) of 0.5.

EXAMPLE 5

The procedure of Example 4 was repeated. However, the yttrium nitrate solution did not contain nitric acid but, in contrast, the ammonium oxalate solution contained 0.2 mol/l of $HNO_3$.

The yttrium oxide obtained after calcination of the ammonium yttrium oxalate had a $S_{50}$ of 2.3 μm and a particle size dispersion index of 0.45.

EXAMPLE 6

The procedure of Example 1 was repeated, but using a solution of soluble salts of rare earths having a concentration of 170 g/l expressed as $RE_2O_3$, 148 g/l ($Y_2O_3$) of which was yttrium nitrate and 22 g/l ($La_2O_3$) of which was lanthanum nitrate.

The solution of precipitation contained 25 g/l of ammonium oxalate.

The amounts of solutions employed were determined such as to provide a $NH_4/RE$ molar ratio of 4.

The precipitate obtained was a yttrium lanthanum ammonium double oxalate.

After calcination at 900° C., a mixed lanthanum and yttrium oxide was obtained which contained 12.6% of $La_2O_3$ and the characteristics of which are reported in Table IV below:

TABLE IV

| Ratio $NH_4/Y$ | [RE] g/l ($RE_2O_3$) | $S_{50}$ μm | Particle size dispersion coefficient (F) |
|---|---|---|---|
| 4 | 10 | 0.85 | 0.68 |
| 4 | 40 | 0.9 | 0.70 |

EXAMPLE 7

An ammonium double oxalate was prepared by continuously mixing a solution of yttrium nitrate having a concentration of 170 g/l (expressed as $Y_2O_3$) with a 25 g/l ammonium oxalate solution.

Thus, the $NH_4/Y$ ratio was 4.75 and the final $Y_2O_3$ concentration was 16 g/l.

The precipitate recovered after separation and washing was a yttrium ammonium double oxalate having an average particle diameter of 1.4 μm and a particle size dispersion coefficient (F) of 0.4.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of rare earth ammonium double oxalate particulates, comprising (a) adding a second solution of a rare earth compound to a first solution containing both oxalate and ammonium ions to form a precipitate of finely divided rare earth ammonium double oxalate particulates having a particle size dispersion coefficient of less than 0.7, and then (b) separating the precipitate thus obtained from such mixed solution.

2. The process as defined by claim 1, said first solution comprising an aqueous solution of ammonium oxalate.

3. The process as defined by claim 1, said first solution comprising an aqueous solution of oxalic acid and an ammonium compound.

4. The process as defined by claim 3, said ammonium compound comprising ammonia, ammonium oxalate, a salt of ammonium and an inorganic acid, or mixture thereof.

5. The process as defined by claim 4, said ammonium compound comprising an ammonium nitrate or an ammonium chloride.

6. The process as defined by claim 1, said first solution comprising an inorganic acid.

7. The process as defined by claim 1, said second solution comprising an aqueous solution of a rare earth salt.

8. The process as defined by claim 7, said rare earth salt comprising a rare earth nitrate, chloride or sulfate, or mixture thereof.

9. The process as defined by claim 1, said second solution comprising an inorganic acid.

10. The process as defined by claim 7, said second solution comprising a solution of yttrium nitrate, europium nitrate, lanthanum nitrate, neodymium nitrate, dysprosium nitrate, cerium nitrate, gadolinium nitrate, terbium nitrate, or mixture thereof.

11. The process as defined by claim 1, wherein the molar ratio $C_2O_4^=/RE$ and $NH_4^+/RE$ upon completion of precipitation is greater than 2.

12. The process as defined by claim 1, wherein in said first solution, the molar ratio $C_2O_4^=/NH_4^+$ is less than 4 and higher than 0.

13. The process as defined by claim 1, either said first or said second solution further comprising an inorganic acid in an amount providing a molar ratio between the anion of the inorganic acid and the oxalate ions of less than 5 in an admixture Of the first solution and the second solution.

14. The process as defined by claim 11, said molar ratio being greater than 2.5.

15. The process as defined by claim 1, comprising continuously adding said second solution to said first solution.

16. A process as defined by claim 1, further comprising calcining the particulates.

17. The process as defined by claim 16, comprising calcining at a temperature ranging from 600° to 1,200° C.

18. The process as defined by claim 17, comprising calcining at a temperature ranging from 800° to 1,000° C.

19. The process as defined in claim 1, further comprising drying said precipitate.

20. The process according to claim 1, wherein the particulates have a particle size of from 0.5 µm to 3 µm.

21. Particulates of a rare earth oxide comprising platelets having an average particle size ranging from 0.5 µm to 3 µm and a particle size dispersion coefficient of less than 0.7.

22. The particulates as defined in claim 21, wherein said average particle size ranges from 0.5 µm to 0.9 µm.

23. Crystalline particulates of an ammonium rare earth double oxalate comprising platelets having an average particle size ranging from 0.5 µm to 3 µm and a particle size dispersion coefficient of less than 0.7.

* * * * *